US012220262B2

(12) United States Patent
Jayaraman et al.

(10) Patent No.: US 12,220,262 B2
(45) Date of Patent: Feb. 11, 2025

(54) SYSTEMS AND METHODS FOR ATRIAL FIBRILLATION (AF) AND CARDIAC DISORDERS DETECTION FROM BIOLOGICAL SIGNALS

(71) Applicant: Tata Consultancy Services Limited, Mumbai (IN)

(72) Inventors: Srinivasan Jayaraman, Bangalore (IN); Joshin Sahadevan, Bangalore (IN); Sundeep Khandelwal, Noida (IN); Ponnuraj Kirthi Priya, Bangalore (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 212 days.

(21) Appl. No.: 17/203,578

(22) Filed: Mar. 16, 2021

(65) Prior Publication Data

US 2021/0290175 A1 Sep. 23, 2021

(30) Foreign Application Priority Data

Mar. 19, 2020 (IN) .............................. 202021011996

(51) Int. Cl.
*A61B 5/00* (2006.01)
*A61B 5/0205* (2006.01)
(Continued)

(52) U.S. Cl.
CPC .......... *A61B 5/7267* (2013.01); *A61B 5/0205* (2013.01); *A61B 5/352* (2021.01);
(Continued)

(58) Field of Classification Search
None
See application file for complete search history.

(56) References Cited

U.S. PATENT DOCUMENTS

2013/0204149 A1* 8/2013 Hwang ................ A61B 5/7275
703/11
2017/0042479 A1* 2/2017 Shimuta ............... A61B 5/6804
(Continued)

OTHER PUBLICATIONS

Christov, Ivaylo et al., "Multi-parametric Analysis for Atrial Fibrillation Classification in ECG Title of the item: Computing in Cardiology", Sep. 2017, Research Gate, https://www.researchgate.net/publication/323572883_Multi-parametric_Analysis_for_Atrial_Fibrillation_Classification_in_ECG/link/5a9e5fb6aca272cd09c277c2/download.

(Continued)

*Primary Examiner* — Sana Sahand
(74) *Attorney, Agent, or Firm* — FINNEGAN, HENDERSON, FARABOW, GARRETT & DUNNER LLP

(57) ABSTRACT

Continuous monitoring of subject's cardiac system using biological signal(s) (BS) during day-to-day activities is essential for managing personal cardiac health/disorders, etc. Conventional systems/methods lack in improvising overall classification results and configured for specific device/signal say ECG or PPG and so on. Present disclosure provides systems and methods for classifying BS obtained from users, wherein BS are preprocessed to obtain filtered signals (FS). Corresponding feature extraction module is utilized for feature set extraction based on features in FS. The feature set is reduced and segmented into test and training data. Biological signal classification model(s) are generated using training data and a BCM is applied on test data to classify biological signals (BS) as one of Atrial Fibrillation (AF), a non-AF, a cardiac arrythmia disorder, or ischemia. Accelerometer features of connected device associated with the users can be obtained to detect activities which in conjunction with the BCM's output improvises above classification.

9 Claims, 8 Drawing Sheets

(51) Int. Cl.
  *A61B 5/352* (2021.01)
  *G16H 40/67* (2018.01)
  *G16H 50/20* (2018.01)
  *G16H 50/30* (2018.01)
  *A61B 5/024* (2006.01)
  *A61B 5/361* (2021.01)

(52) U.S. Cl.
  CPC ............ *G16H 40/67* (2018.01); *G16H 50/20* (2018.01); *G16H 50/30* (2018.01); *A61B 5/02405* (2013.01); *A61B 5/02416* (2013.01); *A61B 5/361* (2021.01); *A61B 2562/0219* (2013.01)

(56) References Cited

U.S. PATENT DOCUMENTS

| | | | | |
|---|---|---|---|---|
| 2020/0093389 A1* | 3/2020 | Henry | .................... | A61B 5/339 |
| 2021/0128004 A1* | 5/2021 | Zhang | .................... | A61B 5/725 |

OTHER PUBLICATIONS

Sahoo, Prasan Kumar et al., "On the Design of an Efficient Cardiac Health Monitoring System Through Combined Analysis of ECG and SCG Signals", Sensor, Jan. 2018, MDPI https://www.researchgate.net/publication/322752368_On_the_Design_of_an_Efficient_Cardiac_Health_Monitoring_System_Through_Combined_Analysis_of_ECG_and_SCG_Signals/link/5a6dad90aca2722c947e6ae3/download.

Friganović, Krešimir et al., "Optimizing the Detection of Characteristic Waves in ECG Based on Processing Methods Combinations", Access, Sep. 2018, vol. 6, IEEE, https://ieeexplore.ieee.org/stamp/stamp.jsp?tp=&arnumber8463463.

Mei, Zhenning et al., "Automatic Atrial Fibrillation Detection Based on Heart Rate Variability and Spectral Features", Access, Sep. 2018, vol. 6, Publisher: IEEE, https://ieeexplore.ieee.org/stamp/stamp.jsp?arnumber=8468160.

* cited by examiner

SYSTEMS AND METHODS FOR ATRIAL FIBRILLATION (AF) AND CARDIAC DISORDERS DETECTION FROM BIOLOGICAL SIGNALS

PRIORITY CLAIM

This U.S. patent application claims priority under 35 U.S.C. § 119 to: India Application No. 202021011996, filed on Mar. 19, 2020. The entire contents of the aforementioned application are incorporated herein by reference.

TECHNICAL FIELD

The disclosure herein generally relates to biological signal analysis, and, more particularly, to systems and methods for Atrial Fibrillation (AF) and cardiac disorders detection from biological signals.

BACKGROUND

Continuous monitoring of cardiac system using biological signal(s) during locomotion or movement or day-to-day activities is essential for managing personal cardiac health, and disorders such as Atrial Fibrillation (AF), arrhythmia, ischemia and the like. Traditionally, adapted methods to characterize a subject's cardiac disorders is established by collecting Electrocardiogram (ECG) in a control environment or conducting a voluntary study such as treadmill test, Holter system (time bound monitoring) and the like. However, trend in use of wearable device(s) can play a vital role; either with a dedicated device (or smart devices) or smartwatch which could contribute towards diagnosis of AF in ambulatory outpatient. In addendum, wearable device(s) would play a significant role from a clinical perspective, as these can contribute in detecting AF or non-AF in high-risk patient and early stage detection of AF or non-AF.

Wearable device adapts various modality, such as ECG (resistive or capacitive), PPG (optical), atrial pulse (piezo, doppler), and radio frequency (RF) to acquire and monitor the biological parameter(s). In the state-of-the-art system, for every signal modality, developing a dedicated cardiac model or statistical model or classifier or matching technique is required. If not, the process of annotation or diagnosis demands a high skilled experts and consumer more time. In few cases such as PPG, atrial pulse and RF based signals there is a huge demand in an expert.

On the other hand, say trending single lead ECG system, the analysis of RR intervals has received the most attention since such information is readily available or R peak signals is dominant. This conventional method for AF detection may many times lead to misclassification or fails to detect AF; when an AF episode is preceded by some other type of arrhythmia, wherein Arrhythmia also functions like AF by contributing towards irregular ventricular rhythm. Therefore, conventional methods as described above are prone to error and demands in improvising overall classification results.

SUMMARY

Embodiments of the present disclosure present technological improvements as solutions to one or more of the above-mentioned technical problems recognized by the inventors in conventional systems. In one aspect, there is provided a processor implemented method for Atrial Fibrillation (AF) and cardiac disorders detection from biological signals. The method comprises acquiring a plurality of biological signals from one or more sensory devices, wherein each of the plurality of biological signals is unique and pertains to one or more corresponding users, and wherein each of the plurality of biological signals is obtained from a corresponding sensory device amongst the one or more sensory devices; pre-processing the obtained plurality of biological signals to obtain a plurality of filtered signals; selecting, one or more feature extraction modules from a plurality of feature extraction modules comprised in a memory, based on one or more features comprised in each of the plurality of filtered signals; extracting, a features set comprising at least one of one or more heart rate variability (HRV) features, one or more f-wave features, and one or more fiducial point features using a corresponding feature extraction module from the one or more feature extraction modules; applying a feature reduction technique on the extracted features set to obtain a reduced features set; segmenting the reduced features set into test data and training data; generating one or more biological signal classification models using the training data; and selecting at least one biological signal classification model (BCM) from the one or more generated biological signal classification models and applying the selected biological signal classification model (BCM) on the test data to classify each of the plurality of biological signals as one of Atrial Fibrillation (AF), a non-AF, a cardiac arrythmia disorder, or ischemia.

In an embodiment, the plurality of biological signals is at least one of electrical signals, a cardiac pulse signal, and an arterial pulse signal.

In an embodiment, the method further comprises obtaining a plurality of accelerometer features from an inbuilt accelerometer or externally connected to a wearable device associated with the one or more users; detecting, using an accelerometer classification model (ACM), one or more activities based on the obtained plurality of accelerometer features; and classifying, using a weighted sum classification model, each of the plurality of biological signals as one of the Atrial Fibrillation (AF), the non-AF, the cardiac arrythmia disorder, or the ischemia based on an output of the at least one selected BCM and the detected one or more activities.

In an embodiment, when the plurality of biological signals comprises an electrocardiogram (ECG) signal, the step of selecting, one or more feature extraction modules from a plurality of feature extraction modules is preceded by identifying a corresponding lead from the ECG signal and correcting the identified lead from the ECG signal.

In an embodiment, the cardiac pulse signal is one of a photoplethysmogram (PPG) signal or an atrial pulse signal.

In another aspect, there is provided a processor implemented system for Atrial Fibrillation (AF) and cardiac disorders detection from biological signals. The system comprises a memory storing instructions; one or more communication interfaces; and one or more hardware processors coupled to the memory via the one or more communication interfaces, wherein the one or more hardware processors are configured by the instructions to: acquire a plurality of biological signals from one or more sensory devices, wherein each of the plurality of biological signals is unique and pertains to one or more corresponding users, and wherein each of the plurality of biological signals is obtained from a corresponding sensory device amongst the one or more sensory devices; pre-process the obtained plurality of biological signals to obtain a plurality of filtered signals; select, one or more feature extraction modules from a plurality of feature extraction modules comprised in a memory, based on one or more features comprised in each of the plurality of filtered signals; extract a features set comprising at least one of one or more heart rate variability (HRV) features, one or more f-wave features, and one or more fiducial point features using a corresponding feature extraction module from the one or more feature extraction modules; apply a feature reduction technique on the extracted features set to obtain a reduced features set; segment the reduced features set into test data and training data; generate one or more biological signal classification models (BCM) using the training data; and select at least one biological signal classification model (BCM) from the one or more generated biological signal classification models and apply the at least one selected biological signal classification model (BCM) on the test data to classify each of the plurality of biological signals as one of Atrial Fibrillation (AF), a non-AF, a cardiac arrythmia disorder, or ischemia as a validation process.

In an embodiment, the plurality of biological signals is at least one of an electrical signals, a cardiac pulse signal, and an arterial pulse signal.

In an embodiment, the one or more hardware processors are further configured to obtain a plurality of accelerometer features from a inbuilt accelerometer or externally connected to a wearable device associated with the one or more users; detect, using an accelerometer classification model (ACM), one or more activities based on the obtained plurality of features; and classifying, using a weighted sum classification model, each of the plurality of biological signals as one of the Atrial Fibrillation (AF), the non-AF, the cardiac arrythmia disorder, or the ischemia based on an output of the at least one selected BCM and the detected one or more activities.

In an embodiment, when the plurality of biological signals comprises an electrocardiogram (ECG) signal, the one or more hardware processors are configured by the instructions to identify a corresponding lead from the ECG signal and correct the identified lead from the ECG signal, prior to selecting, the one or more feature extraction modules from the plurality of feature extraction modules.

In an embodiment, the cardiac pulse signal is one of a photoplethysmogram (PPG) signal or an atrial pulse signal.

In yet another aspect, there are provided one or more non-transitory machine-readable information storage mediums comprising one or more instructions which when executed by one or more hardware processors cause for Atrial Fibrillation (AF) and cardiac disorders detection from biological signals by acquiring a plurality of biological signals from one or more sensory devices, wherein each of the plurality of biological signals is unique and pertains to one or more corresponding users, and wherein each of the plurality of biological signals is obtained from a corresponding sensory device amongst the one or more sensory devices; pre-processing the obtained plurality of biological signals to obtain a plurality of filtered signals; selecting, one or more feature extraction modules from a plurality of feature extraction modules comprised in a memory, based on one or more features comprised in each of the plurality of filtered signals; extracting a features set comprising at least one of one or more heart rate variability (HRV) features, one or more f-wave features, and one or more fiducial point features using a corresponding feature extraction module from the one or more feature extraction modules; applying a feature reduction technique on the extracted features set to obtain a reduced features set; segmenting the reduced features set into test data and training data; generating one or more biological signal classification models (BCM) using the training data; and selecting at least one biological signal classification model from the one or more generated biological signal classification models (BCM) and applying the at least one selected biological signal classification model (BCM) on the test data to classify each of the plurality of biological signals as one of Atrial Fibrillation (AF), a non-AF, a cardiac arrythmia disorder, or ischemia.

In an embodiment, the plurality of biological signals is at least one of an electrical signal, a cardiac pulse signal, and an arterial pulse signal.

In an embodiment, the one or more instructions which when executed by the one or more hardware processors further cause obtaining a plurality of accelerometer features from an inbuilt accelerometer or externally connected to a wearable device associated with the one or more users; detecting, using an accelerometer classification model (ACM), one or more activities based on the obtained plurality of accelerometer features; and classifying, using a weighted sum classification model, each of the plurality of biological signals as one of the Atrial Fibrillation (AF), the non-AF, the cardiac arrythmia disorder, or the ischemia based on an output of the at least one selected BCM and the detected one or more activities.

In an embodiment, when the plurality of biological signals comprises an electrocardiogram (ECG) signal, the step of selecting, one or more feature extraction modules from a plurality of feature extraction modules is preceded by identifying a corresponding lead from the ECG signal and correcting the identified lead from the ECG signal.

In an embodiment, the cardiac pulse signal is one of a photoplethysmogram (PPG) signal or an atrial pulse signal.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
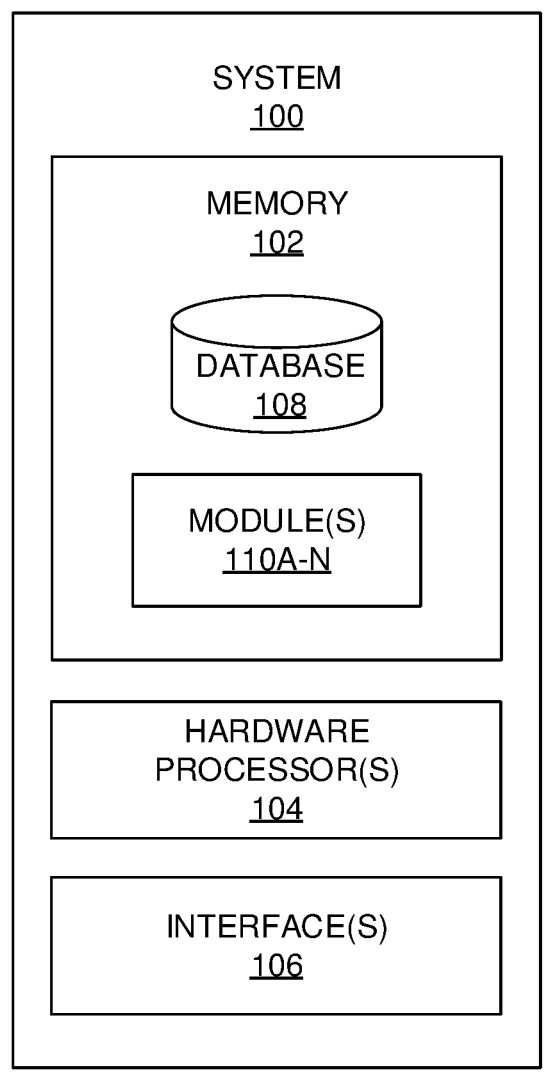
FIG. 1 depicts an exemplary block diagram of a system for the at least one of the Atrial Fibrillation (AF) and cardiac disorders detection from a plurality of biological signals, in accordance with an embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments.

As mentioned above, continuous monitoring of a subject's cardiac system using biological signal(s) during locomotion or movement or day-to-day activities is essential for managing personal cardiac health, disorders such as Atrial Fibrillation (AF), arrhythmia, ischemia and the like. Traditionally, adapted methods to characterize a subject's cardiac disorders is established by collecting Electrocardiogram (ECG) in a control environment or conducting a voluntary study such as treadmill test, Holter system and the like. However, the conventional methods as described above are prone to error and lack in improvising overall classification results. Embodiments of the present disclosure provide systems and methods, wherein any signal type can be received as input to automatically manage and detect AF from various signals such as Electrocardiogram (ECG), photoplethysmogram (PPG) and signal(s) from pulse device with high accuracy. In addendum, automatically handling all these signals in one system is being achieved by system and method of the present disclosure. Further, system of the present disclosure intelligently performs analysis of signals to detect presence (or absence) of specific features in signal and accordingly triggers (or activates) corresponding feature extraction module(s) for extracting various features thereby optimizing system resources (e.g., memory, processor and the like). The extracted features are reduced by applying feature reduction technique(s) and are segmented into test and training data, wherein classification model(s) are generated using the training data for classifying incoming biological signal(s) into AF, non-AF or any cardiac disorder. The system and method of present disclosure further enables automatic detection of a training model to be chosen based on an input signal. System of the present disclosure identifies/detects an inverted R peak and corrects the inverted R peak which leads to improving accuracy of technique(s) implemented by the system.

Referring now to the drawings, and more particularly to FIGS. 1 through 7, where similar reference characters denote corresponding features consistently throughout the figures, there are shown preferred embodiments and these embodiments are described in the context of the following exemplary system and/or method.

FIG. 1 depicts an exemplary block diagram of a system 100 for Atrial Fibrillation (AF) and cardiac disorders detection from biological signals, in accordance with an embodiment of the present disclosure. The system 100 may also be referred as 'classification system', 'Atrial Fibrillation (AF) and cardiac disorders detection system' and may be interchangeably used hereinafter. In an embodiment, the system 100 includes one or more hardware processors 104, communication interface device(s) or input/output (I/O) interface(s) 106 (also referred as interface(s)), and one or more data storage devices or memory 102 operatively coupled to the one or more hardware processors 104. The one or more processors 104 may be one or more software processing components and/or hardware processors. In an embodiment, the hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory. In an embodiment, the system 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, a database 108 is comprised in the memory 102, wherein the database 108 comprises information, for example, various biological signals acquired that are pertaining to one or more users or any other species. The information stored in the database 108 may further comprise filtered biological signals (or filtered signals), features comprised in each of the filtered signals, and the likes. The memory 102 further comprises module(s) 110A-N (e.g., one or more feature extraction modules also referred as 'feature extractor(s)' and may be interchangeably used hereinafter). More specifically, the feature extractors comprise, but are not limited to, a heart rate variability (HRV) feature extraction module 110A, a f-wave feature extraction module 110B, a fiducial feature extraction module 110C and the like.

In an embodiment, the memory 102 may store (or stores) one of more techniques. For instance, one or more feature reduction technique(s), one or more segmentation technique(s) and the like may be comprised in the memory 102 and executed accordingly to perform one or more methodologies described hereinafter. Further the memory 102 may comprise one or more biological signal classification models (also referred as classifiers) which are generated and invoked for execution and which when executed classify the biological signals into Atrial Fibrillation (AF), non-AF and cardiac disorders. The memory 102 further stores (i) accelerometer data obtained from at least one of a wearable device and a connected device (e.g., health monitoring device) associated with the one or more users, (ii) features extracted from the accelerometer data, (iii) detected activities from the features extracted using a weighted sum classification model, wherein the weighted sum classification model is comprised in the memory 102 for execution and detection of the activities, and (iv) classification output of the at least one selected biological classification model based on the detected activities and the output of step 216 as described below, wherein the classification output refers to classification of biological signals into Atrial Fibrillation (AF), non-AF and cardiac disorders. The memory 102 further comprises (or may further comprise) information pertaining to input(s)/output(s) of each step performed by the systems and methods of the present disclosure. In other words, input(s) fed at each step and output(s) generated at each step are comprised in the memory 102 and can be utilized in further processing and analysis.

Figure 2:
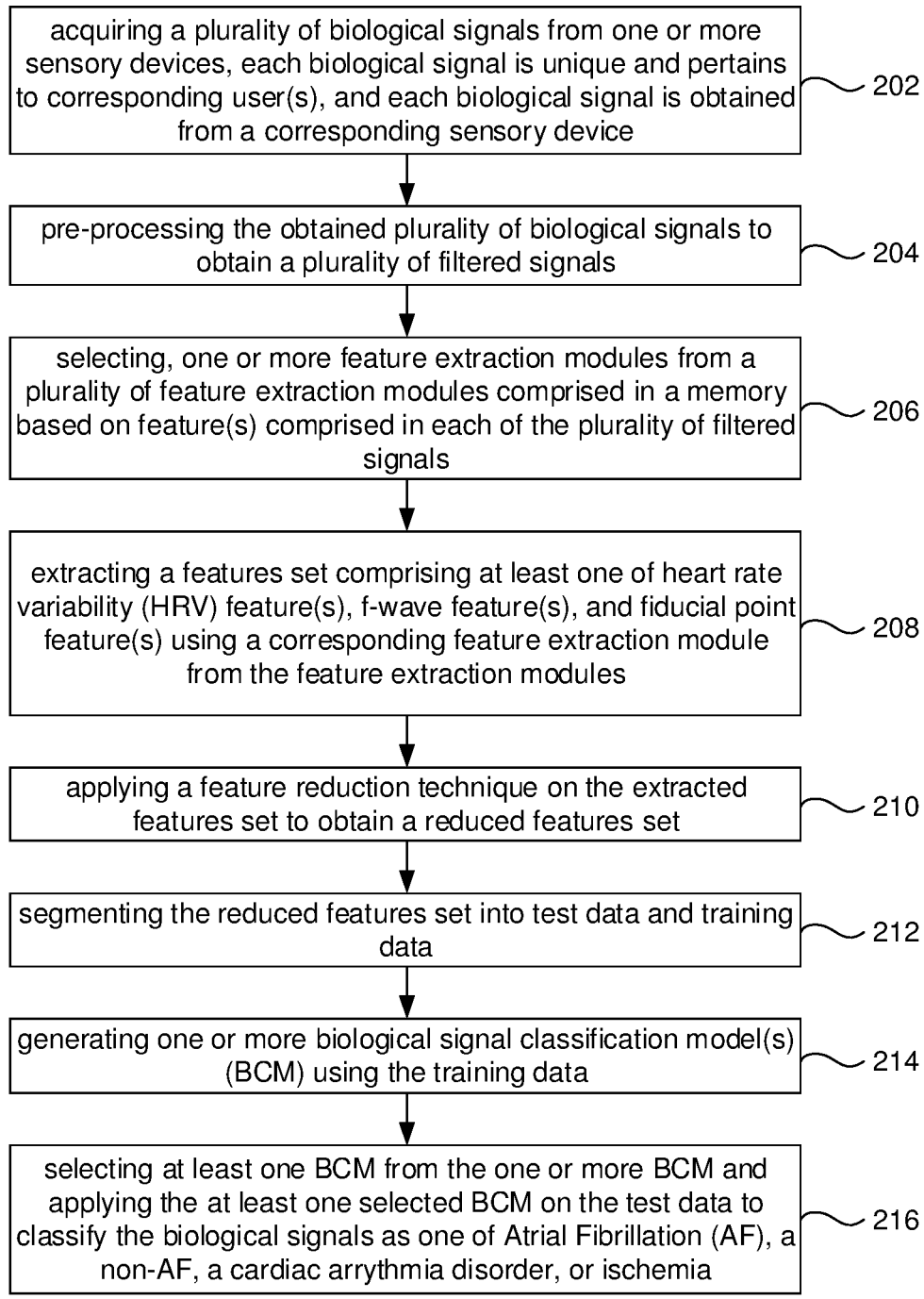
FIG. 2 depicts an exemplary flow chart for the at least one of the Atrial Fibrillation (AF) and cardiac disorders detection from the plurality of biological signals using the system of FIG. 1, in accordance with an embodiment of the present disclosure.

FIG. 2, with reference to FIG. 1, depicts an exemplary flow chart for Atrial Fibrillation (AF) and cardiac disorders detection from biological signals using the system 100 of FIG. 1, in accordance with an embodiment of the present disclosure. In an embodiment, the system(s) 100 comprises one or more data storage devices or the memory 102 operatively coupled to the one or more hardware processors 104 and is configured to store instructions for execution of steps of the method by the one or more processors 104. The steps of the method of the present disclosure will now be explained with reference to components of the system 100 of FIG. 1, the flow diagram as depicted in FIG. 2.

In an embodiment, at step 202 of the present disclosure, the one or more hardware processors 104 acquire a plurality of biological signals from one or more sensory devices. Each of the plurality of biological signals is unique and pertains to one or more corresponding users. Each of the plurality of biological signals is obtained from a corresponding sensory device amongst the one or more sensory devices. For instance, a first biological signal may be acquired from a sensory device say, "device A, pertaining to a user say, 'subject A'. Similarly, a second biological signal may be acquired from a sensory device say, "device B, pertaining to a user say, 'subject B' and so on. In an embodiment, the plurality of biological signals is at least one of an electrical signal, a cardiac pulse signal, and an arterial pulse signal. In an embodiment, the cardiac pulse signal is one of a photoplethysmogram (PPG) signal or an atrial pulse signal. In an example embodiment, the PPG signal is a single lead PPG signal. In another example embodiment, the atrial pulse signal is one of a single or three-lead (3 lead) signal. In yet another example embodiment, the radio frequency (RF) signal is a single lead signal which could be an indirect measure of the arterial pulse signal. In some scenarios, the plurality of biological signals may be a 12 leads signal (e.g., a 12 leads electrocardiogram (ECG) signal).

Further, at step 204 of the present disclosure, the one or more hardware processors 104 pre-process the obtained plurality of biological signals to obtain a plurality of filtered signals. For instance, the plurality of biological signals acquired from the one or more sensory devices corresponding to the one or more users may be raw signals and may contain noisy background. Therefore, the systems and methods of the present disclosure utilize noise reduction technique (comprised in the memory 102) or signal filtering technique (comprised in the memory 102) which when executed filter the obtained plurality of biological signals (or raw signals) and output a plurality of filtered signals. For instance, raw data of mV signal is acquired through surface electrode and amplified to Voltage Signal X(n). Raw signals are pre-processed to obtain filtered signals for further processing.

In an embodiment, at step 206 of the present disclosure, the one or more hardware processors 104 select, one or more feature extraction modules from a plurality of feature extraction modules comprised in the memory 102, based on one or more features comprised in each of the plurality of filtered signals.

In case if any of the plurality of biological signals is one of the photoplethysmogram (PPG) signal or the atrial pulse signal, the step 206 is preceded by pre-processing the photoplethysmogram (PPG) signal or the atrial pulse signal and then steps 206 till 210 are carried out.

Figure 3:
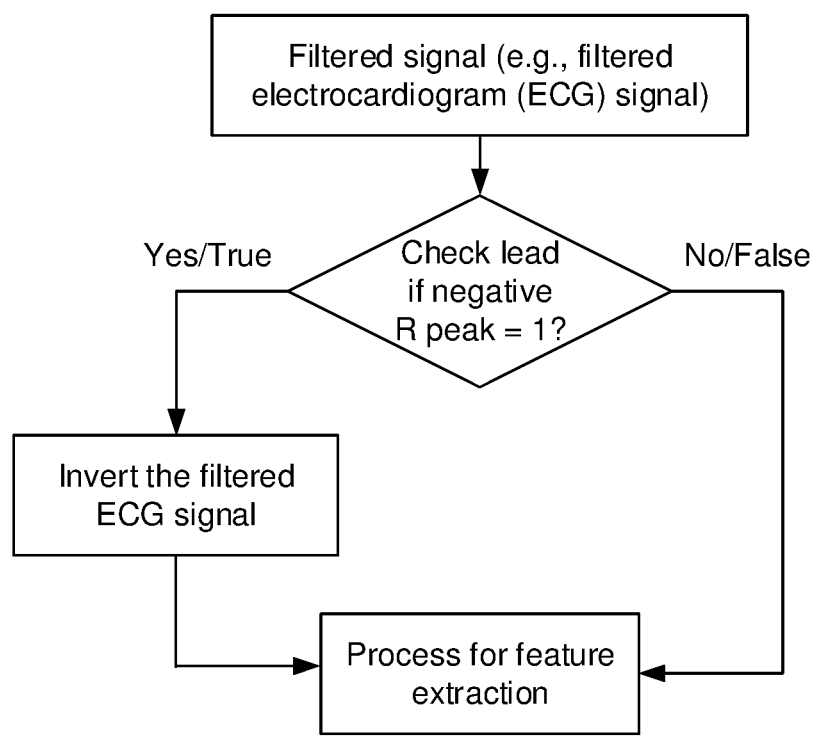
FIG. 3 depicts a flow-chart illustrating a method for a lead identification of an electrical signal (e.g., an electrocardiogram (ECG) signal) and correcting the identified lead thereof in accordance with an embodiment of the present disclosure.
Figure 4:
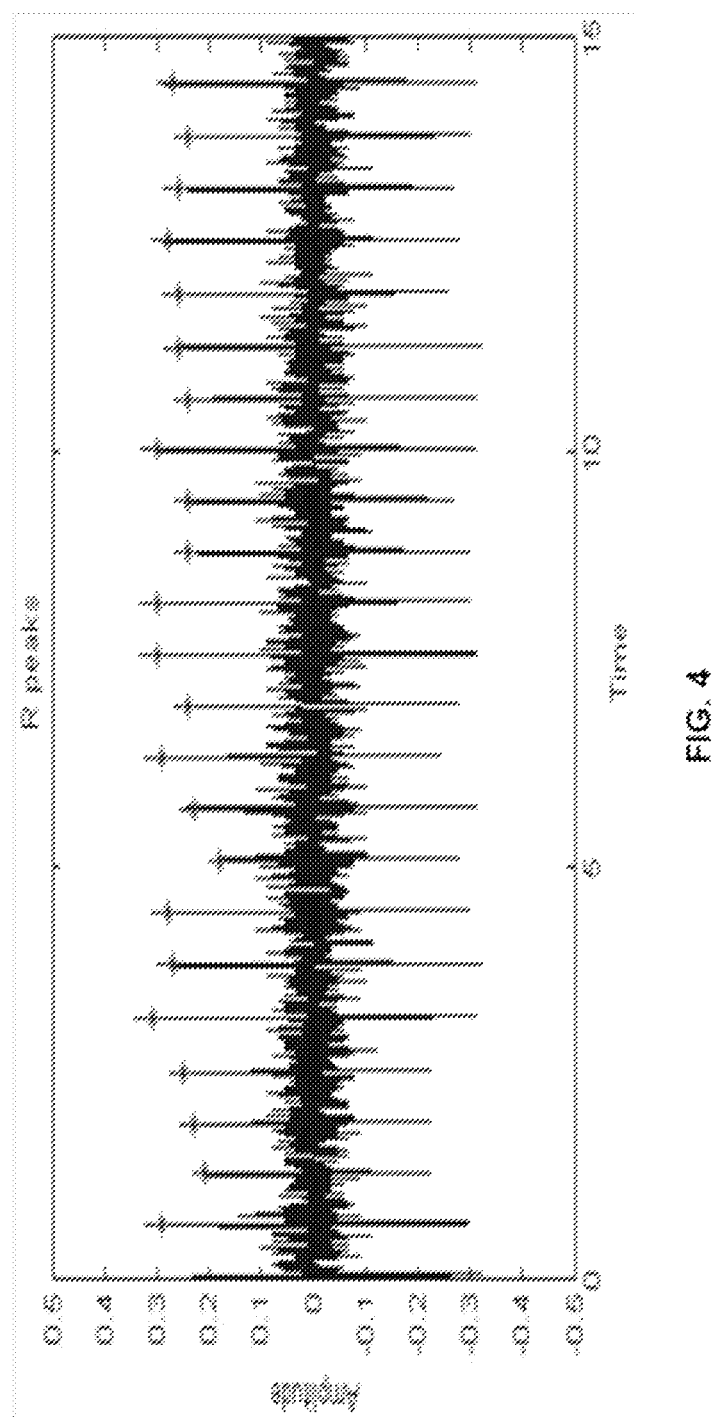
FIG. 4, with reference to FIGS. 1 through 3, depicts a graphical representation of R peak detected in the ECG signal, in accordance with an embodiment of the present disclosure.
Figure 5:
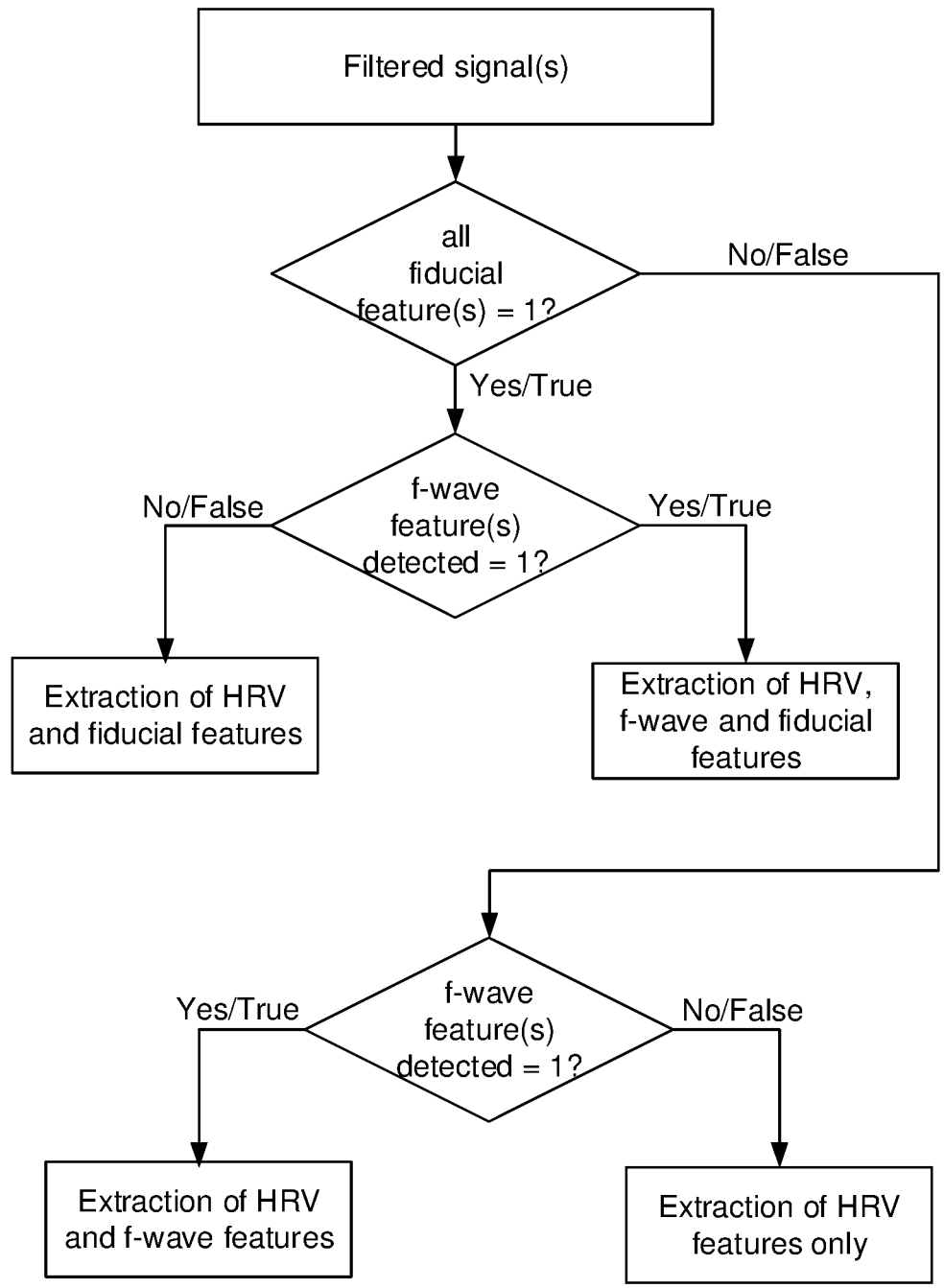
FIG. 5 depicts a flow-chart illustrating a method for selection (or invocation) of feature extraction module(s) (or feature extractor(s)) for extracting one or more features from a plurality of filtered biological signals thereof based on the identified lead, in accordance with an embodiment of the present disclosure.

In case if any of the filtered signals is identified/characterized as electrocardiogram (ECG) signal, the step 206 is preceded by a step where the hardware processors 104 identify a corresponding lead from the ECG signal and the corresponding lead may be further corrected based on the lead type identified in the filtered signal and then steps 206 till 210 are carried out. In other words, the step of identifying a corresponding lead from each of the plurality of filtered signals and correcting the identified lead is based on signal type wherein the signal type is as electrocardiogram (ECG) signal. For instance, assuming one of the filtered signals is an electrical signal such as ECG signal, and if an output from the lead identified results in a R wave inversion, then the lead is corrected for this ECG signal. It is to be understood by a person having ordinary skill in the art and a person skilled in the art that the step of correcting the corresponding lead applies only for an ECG signal type and not for any signal being acquired (e.g., non-ECG signal). FIG. 3, with reference to FIGS. 1 through 2, depicts a flow-chart illustrating a method for a lead identification of an electrical signal (e.g., electrocardiogram (ECG) signal) and correcting the identified lead thereof in accordance with an embodiment of the present disclosure. More specifically, FIG. 3 depicts a filtered ECG signal being received as an input wherein a lead is identified and checked whether negative R peak=1. If negative R peak=1 then the filtered ECG signal corrected by inverting the ECG signal and then sent for further analysis and/or processing (in this case feature extraction process as depicted in FIG. 3). More specifically, FIG. 4, with reference to FIGS. 1 through 3, depicts a graphical representation of R peak detected in the ECG signal, in accordance with an embodiment of the present disclosure. Heart rate variability (HRV) refers to variability in the beat to beat intervals of the heart rate. It essentially reflects changing effect of sympathetic and parasympathetic modulation of autonomic nervous system. Reliability of HRV parameters extracted from ECG signals largely depends on the accuracy of R-peak detection algorithm. In the present disclosure, a modified Pantompkin's algorithm was utilized as known in the art (e.g., refer modified Pan J. and Tompkins W., 1985—N Deepthi and Srinivasan Jayaraman, FIGHT OR FLIGHT CONTROL SYSTEM FOR DRIVERS USING ECG SIGNAL, ICEDSP 2009) for R-peak detection. The detected R peaks are shown in FIG. 4 as mentioned above.

The R-R intervals obtained were checked for missing R-peaks and noisy artifacts by avoiding unusually long and short R-R intervals which are bound to give unreliable results. Equation (1) below shows criteria (or criterion) adopted for RR interval correction for HRV analysis.

$$RR_{Corrected} = \begin{cases} RR_i & \text{if } 0.7 \times \mu_{RR} \leq RR_i \leq 1.5 \times \mu_{RR} \\ \text{ignored} & \text{otherwise} \end{cases} \quad (1)$$

where, $RR_{corrected}$ is the corrected R-R intervals for further analysis, $\mu_{RR}$ is the mean of R-R intervals of 'N' minute ECG record (where N is greater than or equal to 1 minute) and $RR_i$ is the R-R interval under consideration, i=1, 2, 3, ... n, where n=number of RR interval detected in N minutes of ECG record.

In an embodiment, at step 208 of the present disclosure, the one or more hardware processors 104 extract a feature set comprising at least one of one or more HRV features, one or more f-wave features, and one or more fiducial point features using a corresponding feature extraction module from the one or more feature extraction modules. The steps 206 and 208 are better understood by way of method described in a flow-chart depicted in FIG. 5. More specifically, FIG. 5, with reference to FIGS. 1 through 4, depicts a flow-chart illustrating a method for selection of feature extraction module (or feature extractor) for extracting one or more features from the plurality of filtered signals thereof (which could be in some scenarios for instance for ECG signal based on the identified lead), in accordance with an embodiment of the present disclosure. In step 206, the one or more hardware processors 104 select a specific feature extraction module(s) based on features comprised in the plurality of filtered signals, and accordingly only these selected feature extraction modules are utilized (or invoked from the memory 102 and executed) for features set extraction from respective filtered signal(s). For instance, if all fiducial point such as PQRST were being detected then the system 100 selects say, the HRV feature extraction module 110A, the f-wave feature extraction module 110B and the fiducial feature extraction module 110C wherein these modules are turned on or triggered for extracting respective features set from the corresponding filtered signals. On the other hand, if fiducial feature say P wave is missing, then the system 100 turns on or triggers the HRV feature extraction module 110A and the f-wave feature extraction module 110B for extracting respective features set from the corresponding filtered signals and the fiducial feature module(s) 110C or any other feature extraction module 110N may be turned off thus refraining from utilization. Therefore, the duration of PR, QT and so on are not extracted as a feature set. As depicted in FIG. 4, the system 100 checks if all (PQRST) fiducial feature=1. If this condition is true, then the system further checks if f-wave detected=1. If f-wave detected=1 is true then the system 100 selects and triggers the HRV feature extraction module 110A, the f-wave feature extraction module 110B and the fiducial feature extraction module 110C for extracting HRV features, f-wave and fiducial features respectively. In case if the condition f-wave detected=1 is not true (or false), then the system 100 selects (or invokes) and triggers the HRV feature extraction module 110A and the fiducial feature extraction module 110C only for extracting HRV features and fiducial features respectively as only HRV and fiducial features are present in the received filtered signal.

In case if all (PQRST) fiducial feature=1 is not true (or false), then system then the system further checks if f-wave detected=1. If f-wave detected=1 is true, then the system 100 selects (or invokes) and triggers the HRV feature extraction module 110A and the f-wave feature extraction module 110B for extracting HRV features and f-wave features respectively. In case if the condition f-wave detected=1 is not true (or false), then the system 100 selects (or invokes) and triggers the HRV feature extraction module 110A only for extracting HRV features as other features are not present in the received filtered signal.

BioSig tool kit for MATLAB™ which is an open source software library for biomedical signal processing was used for HRV parameters extraction from RR intervals. HRV features are broadly classified into time-domain, geometrical analysis and frequency domain features. Time domain parameters include mean R-R intervals (mean RR), mean heart rate (mean HR), root mean square of standard deviation (RMSSD), standard deviation of R-R intervals (SDNN), number of successive R-R intervals which differ more than 50 ms (NN50count) and percentage (%) of R-R intervals with difference in successive R-R intervals greater than 50 ms (pNN50). Geometrical analysis parameters include HRV Index (bin width of $\frac{1}{128}$s~8 ms). Lastly, the frequency domain features include the power associated with very low frequency (VLF: <0.04 Hz), low frequency (LF: 0.04-0.15 Hz), high frequency (HF: 0.15-0.4 Hz), low to high frequency ratio (LF/HF), normalized power in low frequency (LFnu) and normalized power in high frequency (HFnu).

Figure 6A:
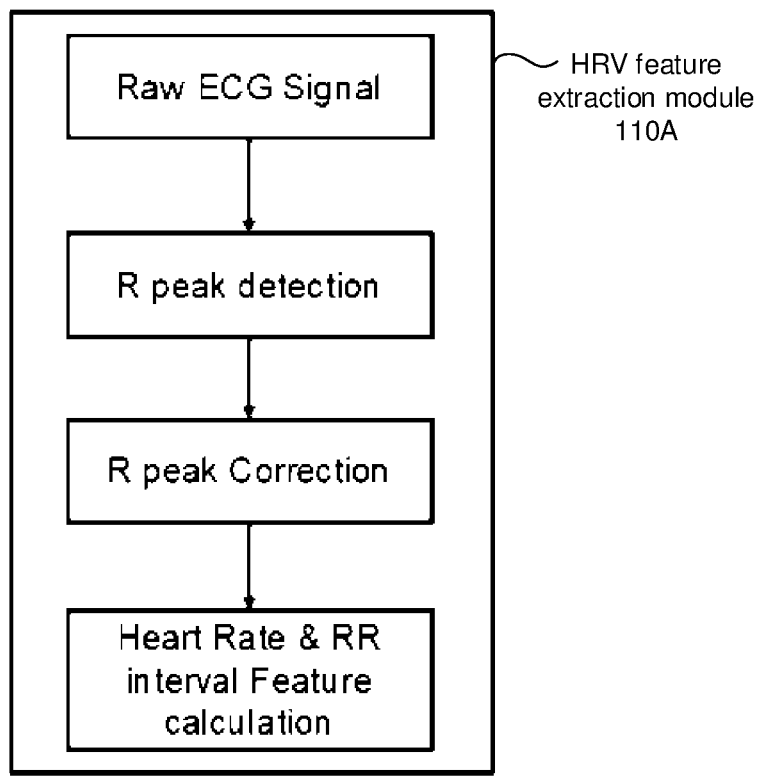
FIG. 6A depict a function block diagram of a Heart rate variability (HRV) feature extraction module comprised in the system of FIG. 1 for extracting HRV features from the plurality of biological signals respectively, in accordance with an embodiment of the present disclosure.
Figure 6B:
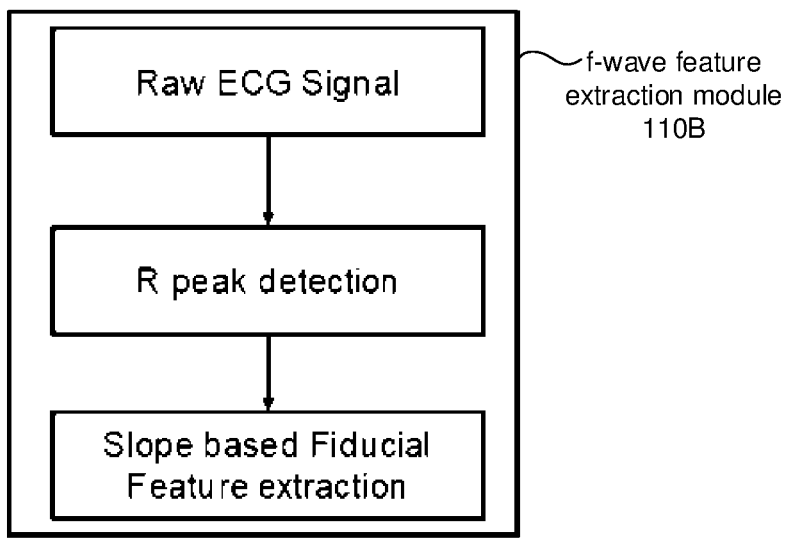
FIG. 6B depict a function block diagram of the Fiducial point feature extraction module comprised in the system of FIG. 1 for extracting Fiducial point features from the plurality of biological signals respectively, in accordance with an embodiment of the present disclosure.
Figure 6C:
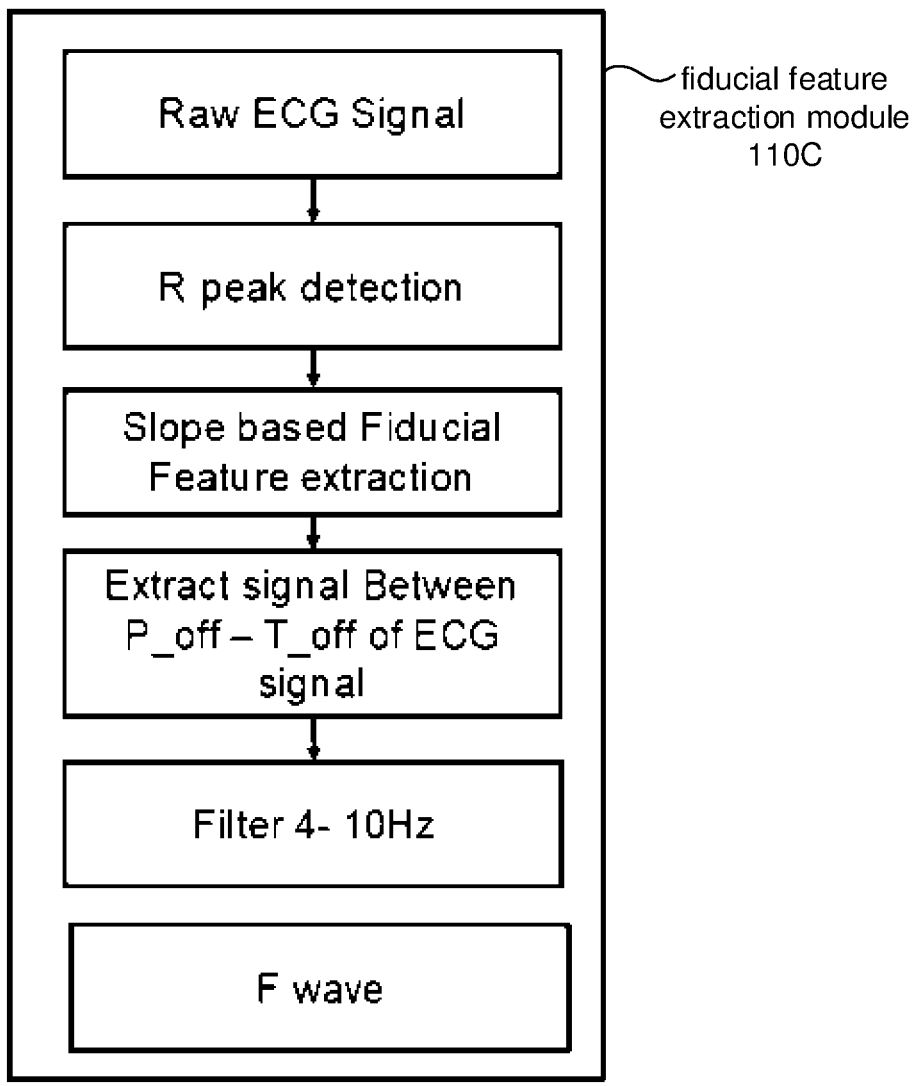
FIG. 6C depict a function block diagram of the F-wave feature extraction module comprised in the system of FIG. 1 for extracting F-wave features from the plurality of biological signals respectively, in accordance with an embodiment of the present disclosure.

FIGS. 6A through 6C, depict a function block diagram of the HRV feature extraction module 110A, the f-wave feature extraction module 110B and the fiducial feature extraction module 110C comprised in the system 100 of FIG. 1 for extracting corresponding features from the plurality of biological signals respectively, in accordance with an embodiment of the present disclosure. More specifically, FIG. 6A depict a function block diagram of the HRV feature extraction module 110A comprised in the system 100 of FIG. 1 for extracting HRV features from the plurality of biological signals respectively, in accordance with an embodiment of the present disclosure. As can be seen from FIG. 6A, a biological signal (e.g., ECG signal) is fed as an input wherein R peaks are detected by a R peak detection block and then the detected R peaks are correction (in case of any errors) by R peak correction block and then Heart Rate and RR interval feature calculation is performed for outputting HRV features. The detected R peaks are depicted in graphical representation of FIG. 6A and the correction is made using the above equation/expression (1).

Examples of HRV features obtained from RR intervals of filtered signal(s) comprise but are not limited to, peak amplitude, frequency at 95 percentile, frequency at 50 percentile, maxPeak, frequency, MPF (mean power frequency), Energy entropy, spectral central frequency, Spectral Central frequency STD, Total harmonic Distortion, MAD of RR, RMSSD, nRMSSD, Wentropy, Pcmean, PCstd, Pcmax, Pcmin, Katz Fractal Dimension, sample entropy, Higuchi Fractal Dimension, MargaosSunKernel entropy, Approximal Entropy, with statistical features like mean, STD, skewness, kurtosis, entropy. RR Interval features such as Mean RR, Mean HR, SDNN, RMSSD, NN50 Count, pNN50, HRV Index, VLF, LF, HF, Total Power, LF/HF ratio, LFnu, HFnu, Poincare's SD1, SD2, Cvrr, CVdrr, median RR, minRR, Rrmax, Sk_RR, Kurt_RR, Range_RR, Var_RR, AFEv, OriginCount, IrrEv, PACEv, DensityEv, AniEV, mean(E_sam), std(E_sam), skewness (E_sam), kurtosis(E_sam), entropy(E_sam), mean(E_apen), std(E_apen), skewness(E_apen), kurtosis(E_apen), entropy (E_apen), E_Disten, mean(alpha2), std(alpha2), skewness (alpha2), kurtosis(alpha2), entropy(alpha2), KFD_F1, Hig_F2, Marg_F3.

Similarly, FIG. 6B depict a function block diagram of the Fiducial point feature extraction module 110B comprised in the system 100 of FIG. 1 for extracting Fiducial point features from the plurality of biological signals respectively, in accordance with an embodiment of the present disclosure. As can be seen from FIG. 6B, a biological signal (e.g., raw ECG signal) is fed as an input into the Fiducial point feature extraction module wherein R peaks are detected by a R peak detection block and slope based Fiducial Feature extraction is performed to output Fiducial point features. The above description of Fiducial point feature extraction is better understood by way of following explanation and example(s):

In Fiducial point feature extraction method, slop of the ECG signal within a window size of 'n' number of samples is evaluated to extract the morphological details. The slope of the signal has both positive and negative values due to increasing and decreasing peaks in an ECG waveform. Slope of the signal is calculated using below exemplary Equation (2):

$$S_{slope}(i)=\tan^{-1}(S(i+n)-S(i))/n \quad (2)$$

where i=1, 2, . . . , N−n, S(t)=extracted ECG Signal with samples 1 to N and n=Window size $S_{slope}(t)$=Slope signal.

The window size depends on the number of samples between the Q peak and R peak in the ECG signal. For finding the window size, the R peak is found by differentiating the ECG signal and the Q wave is detected as the negative peak immediately prior to the detected R peak. The window is placed at the 1st sample and the slope between the 1st and the (n+1)th sample is found and stored. The window is then placed on the 2nd sample and the slope between the 2nd and (n+2)th is found. The window is placed at all samples till the (N−n)th sample and the slope values found is stored as the $S_{slope}$ signal.

A standard range of values is defined for the inclination angle of the P wave, QRS complex and T wave for both normal and abnormal ECG. Thus, from the defined range of slope values for the ECG waveform, the slope values between the minimum positive slope value and the maximum negative slope values are removed to eliminate any noise. For finding the window size, the R peak is found by differentiating the ECG signal and the Q wave is detected as the negative peak immediately prior to the detected R peak. The slope of the signal within this window was found for the entire signal.

The first positive peak was P_on, the first negative peak was P and the following zero crossing was P_off (not shown in FIG.). Similar procedure is followed to identify the Q, R and S peaks and T wave (not shown in FIG.). The features extracted using slope method were then marked on the signal (not shown in FIG.). Accuracy of 97.09% was obtained for this method for a database of 25 patient's digital ECG records.

Examples of fiducial features (also referred as 'morphology features' and may be interchangeably used hereinafter) comprise but are not limited to, 1 min of filtered ECG signal, QRS complex is first detected using Tompkins method (method as known in the art), wherein once the QRS complex is determined, RR interval, Heart rate, Standard deviation (SD) and number of peak in 1 min were calculated. Further, zero crossing was performed on ECG trace to determine an onset and an offset of P, T, Q and S wave. After identifying the onset and offset, a time window was fixed before and after the QRS complex to seek the P wave interval, T wave interval. Based on onset and offset, ST interval, PR interval and QT interval were calculated. From the extracted features, number of R peak and Heart rate were dropped from features vector, as they are dependent on physical conditions of the individuals and they change drastically as well. Feature vector consisted of P wave interval, T wave interval. ST interval, PR interval, QRS complex interval and QT interval.

FIG. 6C depict a function block diagram of the F-wave feature extraction module 110C comprised in the system 100 of FIG. 1 for extracting F-wave features from the plurality of biological signals respectively, in accordance with an embodiment of the present disclosure. As can be seen from FIG. 6C, a biological signal (e.g., raw ECG signal) is fed as an input into the F-wave feature extraction module wherein R peaks are detected by a R peak detection block and slope based Fiducial Feature extraction is performed to output P, Q, R, and T points wherein ECG signal lying between P offset (or P end point and T offset (or T end point) is extracted and filtered between a range of x and y wherein value of x is 4 Hertz and y is 10 Hertz. The output from this filtration step is a F-wave signal wherein the F-wave signal is utilized for F-wave features extraction.

Examples of f-wave features comprise but are not limited to, mean(E_sam), std(E_sam), skewness(E_sam), kurtosis (E_sam), entropy(E_sam), mean(E_apen), std(E_apen), skewness(E_apen), kurtosis(E_apen), entropy(E_apen), E_Disten, mean(alpha2), std(alpha2), skewness(alpha2), kurtosis(alpha2), entropy(alpha2), KFD_F1, Hig_F2, Marg_F3.

Thus, the system 100 intelligently triggers specific feature extraction module(s) for extracting features from respective filtered signals. This ensures that resources of the system 100 such as memory 102 and processor 104 are effectively utilized to perform feature extraction of specific features set based on the features comprised in corresponding filtered signals. This intelligent selection and trigger of specific feature extraction module ensures that memory and processing components of the system (including database where information is queried) are effectively utilized thus optimizing the system 100. In other words, intelligent selection and trigger of specific feature extraction module for feature extraction prevents from causing system overheads that can otherwise degrade performance of the overall system 100. The main objective of selecting specific feature extraction module(s) for feature extraction is to increase accuracy of classification of bio-signals (or also referred as biological signals and interchangeably used hereinafter) and decrease false positive(s).

In an embodiment of the present disclosure, at step 210, the one or more hardware processors 104 apply a feature reduction technique on the extracted features set to obtain a reduced feature set (may also be referred as a set/features set comprising features). In an embodiment of the present disclosure, at step 212, the one or more hardware processors 104 segment the reduced features set into test data and training data. In an embodiment of the present disclosure, at step 214, the one or more hardware processors 104 generate one or more biological signal classification models (BCM) using the training data. Examples of biological signal classification models comprise, but are not limited to, support vector machine (SVM), random forest, or any matching technique. In an embodiment of the present disclosure, at step 216, the one or more hardware processors 104 select at least one biological signal classification model (BCM) from the one or more generated biological signal classification models (BCM) and apply the at least one selected biological signal classification model (BCM) on the test data to classify each of the plurality of biological signals as one of Atrial Fibrillation (AF), a non-AF, a cardiac arrythmia disorder, or ischemia. The above steps 210 till 216 are better understood by way of following experimental results depicted in Table 1:

Experimental Results:

on the training data, one or more classification models were generated. Examples of classification models include but are not limited to CascadeGeneralisation, lazy. LWL and the like. As can be further seen in the above Table 1, of 100 subjects (or users), 47 signals obtained from corresponding users were classified under AF (true positives), 5 were misclassified as non-AF (false positives), 5 were misclassified as AF (true negative), and 43 were classified as non-AF.

Another experiment was conducted for an implant device being operated on a user. It is to be understood and noted by a person having ordinary skill in the art and person skilled in the art that the sensory information from the implant

TABLE 1

| Precision | False positive rate | True positive rate | Classification ethod | K-Fold/80-20 validation | Data_Type |
|---|---|---|---|---|---|
| 0.9 | 0.1 | 0.9 | CascadeGeneralisation | 10-fold validation | Hear rate variability (HRV) |
| 0.9 | 0.1 | 0.9 | lazy.LWL | 10-fold validation | Hear rate variability (HRV) |

| True negative | False positive | True positive | Precision-recall curves | reviewer operating characteristic (ROC area) | Matthew correlation coefficient (MCC) | F-measure | Recall | False negative |
|---|---|---|---|---|---|---|---|---|
| 5 | 5 | 47 | 0.953 | 0.951 | 0.8 | 0.9 | 0.9 | 43 |
| 5 | 5 | 47 | 0.961 | 0.959 | 0.8 | 0.9 | 0.9 | 43 |

As can be seen from above Table 1, HRV features were extracted using the HRV feature extraction module from a biological signal (e.g., refer data_type). Further, feature reduction technique was applied on the HRV features to obtain reduced features set (number of reduced features set not shown in FIGS and above Table 1) and the reduced features set were segmented into test data and training data (segmentation not shown in FIGS and above Table 1). Based on the training data, one or more classification models were generated.

device being captured did not comprise Fiducial point features. Below Table 2 depicts an example of the implant device wherein dataset was obtained, with a sample size of 100, wherein various features were obtained and reduced further for generation of classification models which were applied on the test data for classification of signal(s) obtained from the implant device.

TABLE 2

| Machine learning method | Features reduction minimum redundancy maximum relevancy (mRMR) | No of features | Features set method | Sample size | Dataset |
|---|---|---|---|---|---|
| cascade- CostSensitive Classifier using reweighted training instances and Decision Stump | 150 | | RR Method_1 f-wave RR Method_1 + fw ave (HRV and f-wave) | 100 | Implant device |
| RandomForest - Bagging with 100 iterations and base learner | NA | 44 | RR method1 | | |
| SimpleLogistic Cascade | | 97 | HRV_RR method1 | | |

| | Testing | | Validation | | |
|---|---|---|---|---|---|
| AF termination | Implantable device | | PPV | accuracy | K Fold method |
| | | | 92 | 92 | 10 |
| | | | 86 | 86 | 10 |
| | | | | 89 | 5 |
| | | | | 90 | 10 |

TABLE 2-continued

| Weighted average |
|---|
| TP-0.92, FP-0.085, Precision-0.926, Recall-0. 92, F-0.92, MCC-0. 845, ROC-0. 956. PRC-0.945 |
| TP-0.860, FP-0.139, Precision-0.861, Recall-0.86, F-0.86, MCC-0. 721, ROC-0. 918, PRC-0.918 |
| TP-0.890, FP-0.111, Precision-0.891, Recall-0.89, F-0.89, MCC-0. 780, ROC-0. 931, PRC-0.922 |
| TP-0.90, FP-0.1, Precision-0.91, Recall-0.9, F-0.9, MCC-0. 8, ROC-0. 951, PRC-0.953 |

As can be seen in the above depicted Table 2, various features were extracted from signal(s) obtained the implant device being operated on a user, and feature reduction technique (e.g., a minimum redundancy maximum relevance (mRMR) feature reduction technique, and the like and such examples of the utilizing the feature reduction technique were estimated as depicted in Table 2. Table 2 further depicts weighted average for True positive(s), False positive(s), Precision, Recall, F-Measure (also referred as 'F'), MCC, ROC, and PRC.

Table 3 depicts an example of signal(s) obtained from single-lead ECG.

TABLE 3

| Features set | | | |
|---|---|---|---|
| No of features | method | Sample size | Dataset |
| 8 | RR Method_2 | 5833 | (signals |
| 8 | RR Method_2 | | from |
| 8 | RR Method_2 | | single- |
| 8 | RR Method_2 | | lead ECG) |
| 67 | RR Method_3 | | |

| Testing | Validation | | Machine | Features reduction minimum redundancy maximum |
|---|---|---|---|---|
| Implantable loop | PPV | accuracy | K Fold method | learning method | relevancy (mRMR) |
| 78% | | | | SVM | NA |
| 80% | | | | KNN | NA |
| | 95.2 | 95.21 | 10 | Random Forest | NA |
| | 95.2 | 95.21 | 10 | cost sensitive | NA |
| | 96 | 96 | 10 | cost sensitive | 25 |

| Weighted average | AF termination |
|---|---|
| TP-0.95, FP-0.205, Precision-0.95, Recall-0.95, F-0.95, MCC-0.78, ROC-0.969, PRC-0.979 | |
| TP-0.95, FP-0.205, Precision-0.95, Recall-0.95, F-0.95, MCC-0.78, ROC-0.969, PRC-0.979 | |
| TP-0.96, FP-0.152, Precision-0.96, Recall-0. 961, F-0.961, MCC-0. 826, ROC-0. 985, PRC-0.988 | | shall not be construed as limiting the scope of the present disclosure) was applied on the extracted features to obtain reduced features set as applicable. It is to be understood by person having ordinary skill in the art or person skilled in the art that for RR Method_1+fwave (HRV and f-wave), in case noise is present, then system 100 takes only HRV as f-wave features would be missing in the obtained signal. Various classification models were generated using training data (generated from the obtained signal). Examples of various classification models include but are not limited to, cascade—CostSensitive Classifier using reweighted training instances and Decisioni Stump, RandomForest-Bagging with 100 iterations and base learner, SimpleLogistic, cascade, lazy.LWL and the like. Further validation (e.g., K-fold validation) was performed by applying 5-fold validation, 10-fold validation and the like wherein accuracy and PPV As can be seen in the above depicted Table 2, various features were extracted from signal(s) obtained the implant device being operated on a user, and feature reduction technique (e.g., the minimum redundancy maximum relevance (mRMR) feature reduction technique as mentioned above, and the like and such examples of the utilizing the feature reduction technique by the present disclosure shall not be construed as limiting the scope of the present disclosure) was applied on the extracted features to obtain reduced features set as applicable. Various classification models were generated using training data (generated from the obtained signal). Examples of various classification models include but are not limited to, CostSensitive Classifier SVM, KNN, Random Forest, and the like. Further validation (e.g., K-fold validation) was performed by applying 10-fold validation and the like wherein accuracy and PPV were estimated as depicted in Table 3. Table 3 further depicts weighted average for True positive(s), False positive(s), Precision, Recall, F-Measure (also referred as 'F'), MCC, ROC, and PRC.

Figure 7:
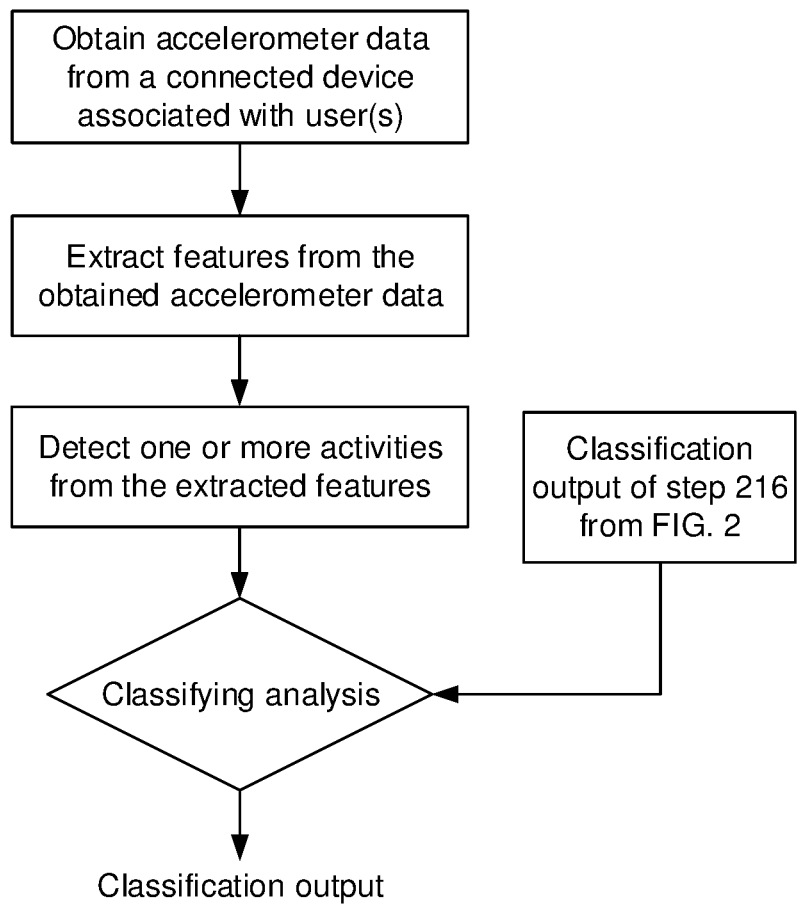
FIG. 7 depicts a flow-chart illustrating a method for incorporating accelerometer data for analysis along with classification output of FIG. 2 for the at least one of the Atrial Fibrillation (AF) and cardiac disorders detection from the plurality of biological signals, in accordance with an embodiment of the present disclosure.

In case based on the above classification of the plurality of biological signals as one of Atrial Fibrillation (AF), a non-AF, a cardiac arrythmia disorder, or ischemia as shown in Table 1 and through experiments depicted in Table 2 and Table 3, if an observation is made that the classification can be further improved, then the system and methods of the present disclosure incorporate analyzing accelerometer data associated with the one or more corresponding users for improving the classification. In other words, a plurality of accelerometer features from an accelerometer are obtained. The accelerometer may be comprised in, or externally connected to a wearable device associated with the one or more users. In other words, the plurality of accelerometer features are obtained from an inbuilt (or inbuild) accelerometer comprised in the wearable device. In another embodiment, the plurality of accelerometer features are obtained from an accelerometer that is externally connected to the wearable device. Further, one or more activities are detected based on the obtained plurality of accelerometer features. In the present disclosure, the detection of activities is performed by using an accelerometer classification model (ACM) comprised in the memory 102. Based on the detected activities and an output of the BCM of step 216, systems and methods employ (or execute) a weighted sum classification model (e.g., a deep weighted classification model and the like wherein the weighted sum classification model is comprised in the memory 102 and invoked for execution as described herein) and such examples of utilizing the classification model by the present disclosure shall not be construed as limiting the scope of the present disclosure) and classify each of the plurality of biological signals as one of the Atrial Fibrillation (AF), the non-AF, the cardiac arrythmia disorder, or the ischemia based on an output of the at least one selected BCM and the detected one or more activities. FIG. 7, with reference to FIGS. 1 through 6C, depicts a flow-chart illustrating a method for incorporating accelerometer data for analysis along with classification output of step 216 of FIG. 2 for at least one of the Atrial Fibrillation (AF) and cardiac disorders detection from the plurality of biological signals, in accordance with an embodiment of the present disclosure. In other words, the systems and methods of the present disclosure may incorporate accelerometer data acquired from wearable devices (e.g., health monitoring device) or connected device (e.g., sensors attached to user's body, or mobile communication device) associated with the users for improvising the classification of the plurality of biological signals as one of Atrial Fibrillation (AF), a non-AF, a cardiac arrythmia disorder, or ischemia. In other words, the prediction accuracy in classification can be improvised by incorporating accelerometer data as and when required depending on the classification output observed in step 216. More specifically, as depicted in FIG. 7, accelerometer data is acquired wherein one or more features are extracted and one or more activities performed by the users are detected using the accelerometer classification model. The detected activities may comprise, but are not limited to, walking, jogging, sitting, standing and the like. The weighted sum classification model is then utilized to classify each of the plurality of biological signals as one of the Atrial Fibrillation (AF), the non-AF, the cardiac arrythmia disorder, or ischemia based on the detected activities and the output of BCM of step 216.

Embodiments of the present disclosure provide systems and methods for automatically detecting (or automatically annotating given physiological (or biological) signals such as ECG, PPG, atrial pulse signal as AF or normal sinus rhythm (or cardiac disorders). Particularly, systems and methods determine the cardiac arrhythmia such as Atrial fibrillation, tachycardia, bradycardia of the vital physiological signal(s) (or biological signals). More specifically, the embodiments of the present disclosure achieve the above automatic detection and classification/annotation by provide systems and methods as depicted in various figures of the present disclosure, wherein a single system can handle ECG (resistive or capacitive), PPG (optical), atrial pulse (piezo, Doppler), and RF to acquire and monitor the physiological (biological) parameter(s). The present disclosure implements the system 100 that is optimized to classify or detect the signal as AF or non-AF or other. Further, the system 100 intelligently performs analysis of signals to detect presence (or absence) of specific features in signal and accordingly triggers (or activates) corresponding feature extraction module(s) for extracting various features thereby optimizing system resources (e.g., memory, processor and the like). The system and method of present disclosure further enables automatic detection of a training model to be chosen based on an input signal (e.g., refer FIG. 5). Furthermore, the ability of the system 100 to identify/detect an inverted R peak and further correct the inverted R peak improves accuracy of technique(s) implemented by the system. Moreover, the systems and methods of the present disclosure has its applicability in various domains, for example, but not limited to, health care, lifestyle, fitness market, automobile industry, medical device manufacturing industry, aviation, railway(s) and the like.

As described, continuous monitoring of subject's cardiac system using biological signal(s) (BS) during day-to-day activities is essential for managing personal cardiac health/disorders, etc. Conventional systems/methods are prone to error, lack in improvising overall classification results and are configured for specific device/signal say ECG or PPG and so on. Present disclosure provides systems and methods for classifying BS obtained from users, wherein BS are preprocessed to obtain filtered signals (FS). Corresponding feature extraction module is utilized for feature set extraction based on features in FS. The feature set is reduced and segmented into test and training data. Biological signal classification model(s) are generated using training data and a BCM is applied on test data to classify biological signals (BS) as one of Atrial Fibrillation (AF), a non-AF, a cardiac arrythmia disorder, or ischemia. Accelerometer features of connected device associated with the users can be obtained to detect activities which in conjunction with the BCM's output improvises above classification.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor implemented method for detection of Atrial Fibrillation (AF) and cardiac disorder from biological signals for managing cardia health or disorders of one or more users during locomotion or movement or day-to-day activities, comprising:

acquiring a plurality of biological signals by sensory devices from the one or more users while the one or more users is performing one or more activities, wherein the sensory devices are implantable devices or pulse device connected to the one more users to capture the plurality of biological signals of the one or more users while performing the one or more activities, wherein each of the plurality of biological signals is unique and pertains to the one or more corresponding users, wherein the plurality of biological signals comprises an electrical signal acquired from a resistive sensor or a capacitive sensor, a cardiac pulse signal acquired from an optical sensor, and an arterial pulse signal acquired from a piezo sensor or doppler, wherein the electrical signal comprises an ECG signal;

pre-processing the obtained plurality of biological signals to obtain a plurality of filtered signals, wherein if the filtered signal is identified as the ECG signal, then identifying a corresponding lead for the ECG signal and checking if negative R peak is present in the filtered ECG signal, and if yes, then correcting the filtered ECG signal by inverting the ECG signal, wherein correction of the ECG signal based on negative R-peak detection provides reliable HRV features extraction from the ECG signal;

if the filtered signal is identified as the ECG signal, and R Peak detected in the ECG signal, then R-R intervals were checked for missing R Peaks and noisy artefacts, and if yes, then the R-R intervals of the ECG signal are corrected to provide a corrected ECG signal for extraction of HRV features;

selecting, automatically one or more feature extraction modules from a plurality of feature extraction modules including a Heart Rate Variability (HRV) feature extraction module, a f-wave feature extraction module and a fiducial feature extraction module, comprised in a memory based on one or more features comprised in each of the plurality of filtered signals by optimizing system resources including the memory and a processor and utilize the system resources to perform feature extraction of specific features set, by, automatically invoking, by the hardware processor, the HRV feature extraction module, the f-wave feature extraction module and the fiducial feature extraction module from the memory by the processor, when all fiducial points including PORST points are present in the biological signal and detects presence of f-wave in the biological signal, automatically invoking, by the hardware processor, the HRV feature extraction module and the f-wave feature extraction module from the memory, when one of a fiducial point is absent in the biological signal and detects presence of the f-wave in the biological signal, and automatically invoking, by the hardware processor, the HRV feature extraction module and the fiducial feature extraction module from the memory, when all the fiducial points are present in the biological signal and detects absence of the f-wave in the biological signal, wherein if the filtered signal is identified as the ECG signal, and R Peak is detected in the ECG signal, then slope based fiducial feature extraction is performed to output the fiducial point features;

wherein if the filtered signal is identified as the ECG signal, and R Peak is detected in the filtered ECG signal, and the filtered ECG signal is fed as an input into the F-wave feature extraction module and when slope based fiducial feature extraction is performed to output P, Q, R, and T points wherein ECG signal lying between P offset or P end point and T offset or T end point is extracted and filtered between a range of x and y wherein value of x is 4 Hertz and y is 10 Hertz, then the output is a F-wave signal, and the F-wave signal is utilized for F-wave features extraction;

dynamically extracting features set comprising at least one of one or more HRV features, one or more f-wave features, and one or more fiducial point features comprising the PQRST points, using the selected feature extraction module, wherein the one or more HRV features refer to variability in beat to beat intervals of the heart rate, essentially reflecting changing effect of sympathetic and parasympathetic modulation of an autonomic nervous system, wherein the one or more fiducial point features are extracted when R Peak are detected from the biological signal and a slope of the biological signal within a window size of 'n' number of samples is evaluated to extract morphological features, wherein the slope includes both positive and negative values due to increasing and decreasing peaks in an ECG waveform, and the window size depends on the number of samples between a Q peak and the R peak in the ECG signal, wherein, for finding the window size, the R peak is found by differentiating the ECG signal and the Q wave is detected as the negative peak immediately prior to the detected R peak, and the window is placed at a $1^{st}$ sample and the slope between the $1^{st}$ sample and $(n+1)^{th}$ sample is found and stored, further the window is placed on a $2^{nd}$ sample and the slope between the $2^{nd}$ sample and $(n+2)^{th}$ is found, wherein the window is placed at all samples till the $(N-n)^{th}$ sample and the slope is found and stored as $S_{slope}$ signal;

applying a feature reduction technique on the extracted features set to obtain a reduced feature set;

segmenting the reduced features set into test data and training data;

generating one or more machine learning models for biological signal classification using the training data;

automatically selecting at least one machine learning model for biological signal classification from the one or more generated machine learning models for biological signal classification based on the input signal and applying the at least one selected machine learning model on the test data to classify each of the plurality of biological signals as one of Atrial Fibrillation (AF), a non-AF, a cardiac arrythmia disorder, or ischemia;

obtaining a plurality of accelerometer features from an inbuilt accelerometer or an externally connected wearable device of the implantable device connected to the one or more users;

automatically detecting, using an accelerometer classification model (ACM), one or more activities of the one or more users based on the obtained plurality of accelerometer features, wherein the detected one or more activities comprises walking, jogging, sitting, standing; and classifying with improvisation, using the weighted sum classification model, each of the plurality of biological signals as one of Atrial Fibrillation (AF), a non-AF, a cardiac arrythmia disorder, or ischemia based on the output of the machine learning model and the detected one or more activities to characterize a cardiac health disorder of the one or more users, continuously monitoring and managing cardiac health of the one or more users via the one or more hardware processors and communication interface or via the wearable device by using the classified biological signal(s) during locomotion or movement or day-to-day activities.

2. The processor implemented method as claimed in claim 1, wherein the cardiac pulse signal is one of a photoplethysmogram (PPG) signal or an atrial pulse signal.

3. The processor implemented method of claim 1, wherein the HRV features obtained from RR intervals of the filtered signal(s) comprise peak amplitude, frequency at 95 percentile, frequency at 50 percentile, maxPeak, frequency, MPF (mean power frequency), energy entropy, spectral central frequency, spectral central frequency STD, total harmonic distortion, MAD of RR, RMSSD, nRMSSD, Wentropy, Pcmean, PCstd, Pcmax, Pcmin, katz fractal dimension, sample entropy, higuchi fractal dimension, MargaosSunKernel entropy, approximal entropy, with statistical features like mean, STD, skewness, kurtosis, entropy, RR interval features such as mean RR, mean HR, SDNN, RMSSD, NN50 count, pNN50, HRV Index, VLF, LF, HF, total power, LF/HF ratio, LFnu, HFnu, Poincare's SD1, SD2, Cvrr, CVdrr, median RR, minRR, Rrmax, Sk_RR, kurt RR, range RR, Var_RR, AFEv, OriginCount, IrrEv, PACEv, DensityEv, AniEV, mean (E_sam), std (E_sam), skewness (E_sam), kurtosis (E_sam), entropy (E_sam), mean (E_apen), std (E_apen), skewness (E_apen), kurtosis (E_apen), entropy (E_apen), E_Disten, mean (alpha2), std (alpha2), skewness (alpha2), kurtosis (alpha2), entropy (alpha2), KFD_F1, Hig_F2, Marg_F3.

4. The processor implemented method of claim 1, wherein identification of fiducial features comprise receiving a filtered ECG signal, detecting QRS complex of the filtered ECG signal, once the QRS complex is determined, calculating RR interval, Heart rate, standard deviation (SD) and number of peak in the filtered ECG signal, further performing zero crossing on the filtered ECG signal to determine an onset and an offset of P, T, Q and S wave of the filtered ECG signal, after identifying the onset and offset, fixing a time window before and after the QRS complex to seek the P wave interval, T wave interval, based on the onset and offset, calculating ST interval, PR interval and QT interval, further extracting number of R peak and dropping heart rate from features vector as they are dependent on physical conditions of the user and change drastically, wherein the feature vector comprises P wave interval, T wave interval, ST interval, PR interval, QRS complex interval and QT interval.

5. The processor implemented method of claim 1, wherein the f-wave features comprise mean (E_sam), std (E_sam), skewness (E_sam), kurtosis (E_sam), entropy (E_sam), mean (E_apen), std (E_apen), skewness (E_apen), kurtosis (E_apen), entropy (E_apen), E_Disten, mean (alpha2), std (alpha2), skewness (alpha2), kurtosis (alpha2), entropy (alpha2), KFD_F1, Hig_F2, Marg_F3.

6. A system, comprising:

a memory storing instructions; and one or more hardware processors coupled to the memory, wherein the one or more hardware processors are configured by the instructions to:

acquire a plurality of biological signals by sensory devices from one or more users while the one or more users is performing one or more activities, wherein the sensory devices are implantable devices or pulse device connected to the one or more users to capture the plurality of biological signals of the one or more users while performing the one or more activities, wherein each of the plurality of biological signals is unique and pertains to one or more corresponding users, wherein the plurality of biological signals comprises an electrical signal acquired from a resistive sensor or a capacitive sensor, a cardiac pulse signal acquired from an optical sensor, and an arterial pulse signal acquired from a piezo sensor or doppler, wherein the electrical signal comprises an ECG signal;

pre-process the obtained plurality of biological signals to obtain a plurality of filtered signals, wherein if the filtered signal is identified as the ECG signal, then identifying a corresponding lead for the ECG signal and checking if negative R peak is present in the filtered ECG signal, and if yes, then correcting the filtered ECG signal by inverting the ECG signal, wherein correction of the ECG signal based on negative R-peak detection provides reliable HRV features extraction from the ECG signal;

if the filtered signal is identified as the ECG signal, and R Peak detected in the ECG signal, then R-R intervals were checked for missing R Peaks and noisy artefacts, and if yes, then the R-R intervals of the ECG signal are corrected to provide a corrected ECG signal for extraction of HRV features;

select automatically, one or more feature extraction modules from a plurality of feature extraction modules, including a Heart Rate Variability (HRV) feature extraction module, a f-wave feature extraction module and a fiducial feature extraction module, comprised in the memory based on one or more features comprised in each of the plurality of filtered signals by optimizing system resources including the memory and a processor and utilize the system resources to perform feature extraction of specific features set, by, automatically invoking, by the hardware processor, the HRV feature extraction module, the f-wave feature extraction module and the fiducial feature extraction module from the memory by the processor, wherein when all fiducial points including PORST waves are present in the biological signal and detects presence of f-wave in the biological signal, automatically invoking, by the hardware processor, the HRV feature extraction module and the f-wave feature extraction module from the memory, wherein when one of a fiducial point is absent in the biological signal and detects presence of the f-wave in the biological signal, and automatically invoking, by the hardware processor, the HRV feature extraction module and the fiducial feature extraction module from the memory, when all the fiducial points are present in the biological signal and detects absence of the f-wave in the biological signal, wherein if the filtered signal is identified as the ECG signal, and R Peak is detected in the ECG signal, then slope based fiducial feature extraction is performed to output the fiducial point features;

wherein if the filtered signal is identified as the ECG signal, and R Peak is detected in the filtered ECG signal, and the filtered ECG signal is fed as an input into the F-wave feature extraction module and when slope based fiducial feature extraction is performed to output P, Q, R, and T points wherein ECG signal lying between P offset or P end point and T offset or T end point is extracted and filtered between a range of x and y wherein value of x is 4 Hertz and y is 10 Hertz, then the output is a F-wave signal, and the F-wave signal is utilized for F-wave features extraction;

dynamically extract, features set comprising at least one of one or more HRV features, one or more f-wave features, and one or more fiducial point features comprising the PORST points, using the selected feature extraction module, wherein the one or more HRV features refer to variability in beat to beat intervals of the heart rate, essentially reflecting changing effect of sympathetic and parasympathetic modulation of an autonomic nervous system, wherein the one or more fiducial point features are extracted when R Peak are detected from the biological signal and a slope of the biological signal within a window size of 'n' number of samples is evaluated to extract morphological features, wherein the slope includes both positive and negative values due to increasing and decreasing peaks in an ECG waveform, and the window size depends on the number of samples between a Q peak and the R peak in the ECG signal, wherein, for finding the window size, the R peak is found by differentiating the ECG signal and the Q wave is detected as the negative peak immediately prior to the detected R peak, and the window is placed at a $1^{st}$ sample and the slope between the $1^{st}$ sample and $(n+1)^{th}$ sample is found and stored, further the window is placed on a $2^{nd}$ sample and the slope between the $2^{nd}$ sample and $(n+2)^{th}$ is found, wherein the window is placed at all samples till the $(N-n)^{th}$ sample and the slope is found and stored as $S_{slope}$ signal;

apply a feature reduction technique on the extracted features set to obtain one or more reduced features sets;

segment the reduced features set into test data and training data;

generating one or more machine learning models for biological signal classification using the training data;

automatically select at least one machine learning models for biological signal classification from the one or more generated machine learning models for biological signal classification based on the input signal and applying the at least one selected machine learning on the test data to classify each of the plurality of biological signals as one of Atrial Fibrillation (AF), a non-AF, a cardiac arrythmia disorder, or ischemia;

obtain a plurality of accelerometer features from an inbuilt accelerometer or an externally connected wearable device of the implantable device connected to the one or more users;

automatically detect, using an accelerometer classification model (ACM), one or more activities of the one or more users based on the obtained plurality of accelerometer features, wherein the detected one or more activities comprises walking, jogging, sitting, standing; and classify with improvisation, using the weighted sum classification model, each of the plurality of biological signals as one of Atrial Fibrillation (AF), a non-AF, a cardiac arrythmia disorder, or ischemia based on the output of machine learning model and the detected one or more activities to characterize a cardiac health disorder of the one or more users, and continuously monitor and manage cardiac health of the one or more users via the one or more hardware processors and communication interface or via the wearable device by using the classified biological signal(s) during locomotion or movement or day-to-day activities.

7. The system as claimed in claim 6, wherein the cardiac pulse signal is one of a photoplethysmogram (PPG) signal or an atrial pulse signal.

8. One or more non-transitory machine-readable information storage mediums comprising one or more instructions which when executed by one or more hardware processors cause for Atrial Fibrillation (AF) and cardiac disorders detection from biological signals by:

acquiring a plurality of biological signals by one or more sensory devices from one or more users while the one or more users is performing one or more activities, wherein the one or more sensory devices are implantable devices or pulse device connected to the one more users to capture the plurality of biological signals of the one or more users while performing the one or more activities, wherein each of the plurality of biological signals is unique and pertains to the one or more corresponding users, wherein the plurality of biological signals comprises an electrical signal acquired from a resistive sensor or a capacitive sensor, a cardiac pulse signal acquired from an optical sensor, and an arterial pulse signal acquired from a piezo sensor or doppler, wherein the electrical signal comprises an ECG signal;

pre-processing the obtained plurality of biological signals to obtain a plurality of filtered signals, wherein if the filtered signal is identified as the ECG signal, then identifying a corresponding lead for the ECG signal and checking if negative R peak is present in the filtered ECG signal, and if yes, then correcting the filtered ECG signal by inverting the ECG signal, wherein correction of the ECG signal based on negative R-peak detection provides reliable HRV features extraction from the ECG signal;

if the filtered signal is identified as the ECG signal, and R Peak detected in the ECG signal, then R-R intervals were checked for missing R Peaks and noisy artefacts, and if yes, then the R-R intervals of the ECG signal are corrected to provide a corrected ECG signal for extraction of HRV features;

selecting, automatically one or more feature extraction modules from a plurality of feature extraction modules including a Heart Rate Variability (HRV) feature extraction module, a f-wave feature extraction module and a fiducial feature extraction module, comprised in a memory based on one or more features comprised in each of the plurality of filtered signals by optimizing system resources including the memory and a processor and utilize the system resources to perform feature extraction of specific features set, by, automatically invoking, by the hardware processor, the HRV feature extraction module, the f-wave feature extraction module and the fiducial feature extraction module from the memory by the processor, when all fiducial points including PQRST waves are present in the biological signal and detects presence of f-wave in the biological signal, automatically invoking, by the hardware processor, the HRV feature extraction module and the f-wave feature extraction module from the memory, wherein when one of a fiducial point is absent in the biological signal and detects presence of the f-wave in the biological signal, and automatically invoking, by the hardware processor, the HRV feature extraction module and the fiducial feature extraction module from the memory, when all the fiducial points are present in the biological signal and detects absence of the f-wave in the biological signal, wherein if the filtered signal is identified as the ECG signal, and R Peak is detected in the ECG signal, then slope based fiducial feature extraction is performed to output the fiducial point features;

wherein if the filtered signal is identified as the ECG signal, and R Peak is detected in the filtered ECG signal, and the filtered ECG signal is fed as an input into the F-wave feature extraction module and when slope based fiducial feature extraction is performed to output P, Q, R, and T points wherein ECG signal lying between P offset or P end point and T offset or T end point is extracted and filtered between a range of x and y wherein value of x is 4 Hertz and y is 10 Hertz, then the output is a F-wave signal, and the F-wave signal is utilized for F-wave features extraction;

dynamically extracting features set comprising at least one of one or more HRV features, one or more f-wave features, and one or more fiducial point features comprising the PQRST points, using the selected feature extraction module, wherein the one or more HRV features refer to variability in beat to beat intervals of the heart rate, essentially reflecting changing effect of sympathetic and parasympathetic modulation of an autonomic nervous system, wherein the one or more fiducial point features are extracted when R Peak are detected from the biological signal and a slope of the biological signal within a window size of 'n' number of samples is evaluated to extract morphological features, wherein the slope includes both positive and negative values due to increasing and decreasing peaks in an ECG waveform, and the window size depends on the number of samples between a Q peak and the R peak in the ECG signal, wherein, for finding the window size, the R peak is found by differentiating the ECG signal and the Q wave is detected as the negative peak immediately prior to the detected R peak, and the window is placed at a $1^{st}$ sample and the slope between the $1^{st}$ sample and $(n+1)^{th}$ sample is found and stored, further the window is placed on a $2^{nd}$ sample and the slope between the $2^{nd}$ sample and $(n+2)^{th}$ is found, wherein the window is placed at all samples till the $(N-n)^{th}$ sample and the slope is found and stored as $S_{slope}$ signal;

applying a feature reduction technique on the extracted features set to obtain a reduced feature set;

segmenting the reduced features set into test data and training data;

generating one or more machine learning models for biological signal classification using the training data;

automatically selecting at least one machine learning model for biological signal classification from the one or more generated machine learning models for biological signal classification based on the input signal and applying the at least one selected machine learning model on the test data to classify each of the plurality of biological signals as one of Atrial Fibrillation (AF), a non-AF, a cardiac arrythmia disorder, or ischemia;

obtaining a plurality of accelerometer features from an inbuilt accelerometer or an externally connected to a wearable device of the implantable device connected to the one or more users;

automatically detecting, using an accelerometer classification model (ACM), one or more activities of the one or more users based on the obtained plurality of accelerometer features, wherein the detected one or more activities comprises walking, jogging, sitting, standing; and classifying with improvisation, using the weighted sum classification model, each of the plurality of biological signals as one of Atrial Fibrillation (AF), a non-AF, a cardiac arrythmia disorder, or ischemia based on the output of the machine learning model and the detected one or more activities to characterize a cardiac health disorder of the one or more users, and continuously monitoring and managing cardiac health of the one or more users via the one or more hardware processors and communication interface or via the wearable device by using the classified biological signal(s) during locomotion or movement or day-to-day activities.

9. The one or more non-transitory machine-readable information storage mediums of claim 8, wherein the cardiac pulse signal is one of a photoplethysmogram (PPG) signal or an atrial pulse signal.

\* \* \* \* \*